(12) United States Patent
Wiley et al.

(10) Patent No.: US 9,592,927 B2
(45) Date of Patent: Mar. 14, 2017

(54) OVERPACK SALVAGE DRUM AND RELATED METHODS

(71) Applicant: ENPAC, L.L.C., Eastlake, OH (US)

(72) Inventors: Jay Wiley, Mentor, OH (US); Lawrence Stanek, Akron, OH (US); Scott R. Janda, Chagrin Falls, OH (US); Timothy D. Reed, Northfield Center, OH (US)

(73) Assignee: ENPAC, L.L.C., Eastlake, OH (US)

( * ) Notice: Subject to any disclaimer, the term of this patent is extended or adjusted under 35 U.S.C. 154(b) by 23 days.

(21) Appl. No.: 14/669,974

(22) Filed: Mar. 26, 2015

(65) Prior Publication Data

US 2015/0274377 A1   Oct. 1, 2015

Related U.S. Application Data

(60) Provisional application No. 61/971,287, filed on Mar. 27, 2014.

(51) Int. Cl.

| | |
|---|---|
| *B65D 21/036* | (2006.01) |
| *B65D 8/00* | (2006.01) |
| *B65D 6/38* | (2006.01) |
| *B65D 21/02* | (2006.01) |
| *B65D 43/02* | (2006.01) |

(52) U.S. Cl.
CPC .............. *B65D 11/06* (2013.01); *B65D 11/24* (2013.01); *B65D 21/022* (2013.01); *B65D 43/0231* (2013.01); *B65D 2543/00027* (2013.01); *B65D 2543/00092* (2013.01); *B65D 2543/00222* (2013.01); *B65D 2543/00296* (2013.01); *B65D 2543/00537* (2013.01); *Y10T 29/49826* (2015.01)

(58) Field of Classification Search
CPC .............. B65D 21/022; B65D 21/0219; B65D 21/0217; B65D 2543/00537; B65D 43/0231; B65D 11/06; B65D 2543/00027
USPC ........................................................ 206/508
See application file for complete search history.

(56) References Cited

U.S. PATENT DOCUMENTS

| | | | |
|---|---|---|---|
| 4,034,886 A * | 7/1977 | Galer ................. | B65D 21/0219 206/508 |
| 4,708,258 A | 11/1987 | Shaw et al. | |
| 5,025,926 A * | 6/1991 | Gregerson ........ | H01L 21/67369 206/454 |
| 8,281,948 B2 | 10/2012 | Stanek et al. | |

(Continued)

*Primary Examiner* — Stephen Castellano
(74) *Attorney, Agent, or Firm* — Rankin, Hill & Clark LLP

(57) ABSTRACT

An overpack salvage drum including a drum body and a lid. A bottom wall and side wall of the drum body cooperate to define an interior of the drum body. The lid is configured to close an open top of the drum body. The lid includes at least two independent lid threads to engage with corresponding independent drum threads provided on the drum body. The lid includes a plurality of alternating castellations having a flat inner facing side and castellations having an arcuate inner facing side, which can be interdigitated with castellations on another lid when two lids are stacked together, or can be used to lock with a drum body to rotationally secure a drum body relative to the lid when in a stacked arrangement. The lids include lugs and recesses, or rings that allow for secure stacking of the lids.

14 Claims, 5 Drawing Sheets

(56) References Cited

U.S. PATENT DOCUMENTS

2004/0089658 A1* 5/2004 Sarnoff .................. B65D 1/34
  220/4.24
2008/0308555 A1* 12/2008 Stolzman ................ B65D 1/16
  220/288

* cited by examiner

OVERPACK SALVAGE DRUM AND RELATED METHODS

This application claims benefit of provisional application Ser. No. 61/971,287 filed Mar. 27, 2014.

BACKGROUND OF INVENTION

Field of Invention

The present invention relates to overpack salvage drums and related methods. More particularly, the present invention relates to overpack salvage drums and related methods that exhibit improved sealing, stacking and manufacturing characteristics.

Description of Related Art

The U.S. Department of Transportation ("USDOT") and the United Nations ("UN") have established regulations for removable head salvage drums (see, e.g., 49 C.F.R. §173.3 (c)), which are also known in the art and hereinafter referred to as overpack salvage drums. Overpack salvage drums are used in a variety of applications, including for the containment of packages that have been damaged, have otherwise become defective or have been found to be leaking, and/or for the containment of potentially hazardous solid materials while they are being transported. Shaw et al., U.S. Pat. No. 4,708,258, discloses a rotationally molded polyethylene overpack salvage drum that meets such USDOT and UN standards.

The overpack salvage drum according to Shaw et al. includes a single-walled drum body having an open end and a double-walled lid that is adapted to threadingly engage the open end of the drum body and thereby seal and contain a steel drum therein. A closed-cell foam gasket in the lid seals the closure between the lid and the drum body. The present invention improves upon the basic design of the overpack salvage drum disclosed by Shaw et al.

BRIEF SUMMARY OF THE INVENTION

The difficulties and drawbacks associated with previously known overpack salvage drums and overpacking strategies are addressed in the present overpack salvage drums and methods.

The present subject matter relates to overpack salvage drums and related methods. The overpack salvage drums include a drum body and a lid selectively engageable to the drum body for closing the overpack salvage drum and for containing an associated package in the interior of the drum body.

Throughout the instant specification and in the appended claims, the term "package" thus refers to any solid or liquid material that may be contained within the overpack salvage drum including, but not limited to, containers (e.g., metal drums or plastic drums etc.) that may contain liquids or solids or a combination of liquids and solids, solid manufactured parts (e.g., piping and fittings etc.) and other solid or liquid materials (e.g., contaminated soils, absorbent materials, etc.).

The lid can be selectively engaged to the drum body using one or more threads on the drum body having a complimentary fitting shape to corresponding threads on the lid. When the lid is threadingly engaged to the drum body, the lid seals the package in the interior of the drum body.

The lid includes a plurality of castellations on an upper side thereof, which are spaced apart to thereby define gaps between the castellations. The castellations can be used in order to open or close the overpack salvage drum, wherein a beam can be inserted in the gaps to be used as a lever to help rotationally move the lid relative the drum body.

When one overpack salvage drum is stacked on another, the castellations on the lid of a lower overpack salvage drum can also be used for engaging recesses in a drum body of an upper overpack salvage drum. Such engagement centers the upper overpack salvage drum in relation to the lower overpack salvage drum to prevent tipping, and also rotationally secures or locks the upper overpack salvage drum in relation to the lower overpack salvage drum to inhibit rotational movement of the two overpack salvage drums relative to each other.

The castellations are also configured on the lids in such a manner so that castellations from two lids can be mated to each other in an interlocking manner (i.e. castellations of one lid fitting in the gaps between castellations on the other lid and vice versa). When multiple lids are stacked one on the other with castellations on the lids facing each other, the interlocking castellations allow the lids to occupy less vertical space than if the castellations did not interlock.

A bottom peripheral edge of the lids can also include one or more lugs and one or more corresponding lug recesses with interlocking geometry, or other interlocking geometry. When multiple lids are stacked one on the other with bottom peripheral edges on the lids facing each other, the lug(s) on one lid are configured to be received inside the lug recess(es) of another lid. The mated lugs and lug recesses, as well as the interlocking castellations inhibit stacked lids from moving horizontally relative to each other.

In one aspect, the present subject matter provides an overpack salvage drum comprising a drum body and a lid. The drum body includes a bottom wall, a side wall, and an open top. The bottom wall and side wall cooperate to define an interior volume of the drum body. The lid configured to close the open top of the drum body. The lid includes a plurality of castellations that extend upwardly from a top side of the lid. The plurality of castellations are arranged circumferentially at a periphery of the top side of the lid and are separated from each other by gaps. When the top side of the lid is viewed in plan, the gaps separating the plurality of castellations have a larger circumferential dimension than the plurality of castellations.

In another aspect, the present subject matter provides a stack of overpack salvage drums including a first overpack salvage drum and a second overpack salvage drum. The first overpack salvage drum includes a first drum body and a first lid. The first drum body includes a bottom wall, a side wall, a plurality of recesses in the side wall, and an open top. The first lid is configured to close the open top of the first drum body. The first lid includes a plurality of castellations that extend upwardly from a top side of the first lid. The plurality of castellations are arranged circumferentially at a periphery of the top side of the first lid and are separated from each other by gaps. When the top side of the first lid is viewed in plan, the gaps separating the plurality of castellations have a larger circumferential dimension than the plurality of castellations. The second overpack salvage drum includes a second drum body and a second lid. The second drum body includes a bottom wall, a side wall, a plurality of recesses in the side wall, and an open top. The second lid is configured to close the open top of the second drum body. The second lid includes a plurality of castellations that extend upwardly from a top side of the second lid. The plurality of castellations are arranged circumferentially at a periphery of the top side of the second lid and are separated from each other by gaps. When the top side of the second lid is viewed in plan, the gaps separating the plurality of castellations have a larger circumferential dimension than the plurality of castellations.

In another aspect, the present subject matter provides a method of stacking overpack salvage drums including a first overpack salvage drum and a second overpack salvage drum. The first overpack salvage drum includes a first drum body and a first lid. The first drum body includes a bottom wall, a side wall, a plurality of recesses in the side wall, and an open top. The bottom wall and side wall cooperate to define an interior volume of the first drum body. The first lid is configured to close the open top of the first drum body and includes a plurality of castellations that extend upwardly from a top side of the first lid. The plurality of castellations are arranged circumferentially at a periphery of the top side of the first lid and are separated from each other by gaps. When the top side of the first lid is viewed in plan, the gaps separating the plurality of castellations have a larger circumferential dimension than the plurality of castellations. The second overpack salvage drum includes a second drum body and a second lid. The second drum body includes a bottom wall, a side wall, a plurality of recesses in the side wall, and an open top. The bottom wall and side wall cooperate to define an interior volume of the second drum body. The second lid is configured to close the open top of the second drum body and includes a plurality of castellations that extend upwardly from a top side of the second lid. The plurality of castellations are arranged circumferentially at a periphery of the top side of the second lid and are separated from each other by gaps. When the top side of the second lid is viewed in plan, the gaps separating the plurality of castellations have a larger circumferential dimension than the plurality of castellations. The method comprises stacking the first and second drum bodies such that the first drum body is nested in the interior of the second drum body to thereby define a drum body stack. The method also includes stacking the first and second lids to thereby define a lid stack.

The foregoing and other features of the invention are hereinafter more fully described and particularly pointed out in the claims, the following description setting forth in detail certain illustrative embodiments of the invention, these being indicative, however, of but a few of the various ways in which the principles of the present subject matter may be employed.

As will be realized, the subject matter described herein is capable of other and different embodiments and its several details are capable of modifications in various respects, all without departing from the claimed subject matter. Accordingly, the drawings and description are to be regarded as illustrative and not restrictive.

BRIEF DESCRIPTION OF THE DRAWINGS

These, as well as other features, aspects, and advantages of the present subject matter, will be more completely understood and appreciated by referring to the following more detailed description of the exemplary embodiments of the present subject matter in conjunction with the accompanying drawings.

DETAILED DESCRIPTION OF THE INVENTION

Figures 1, 2:
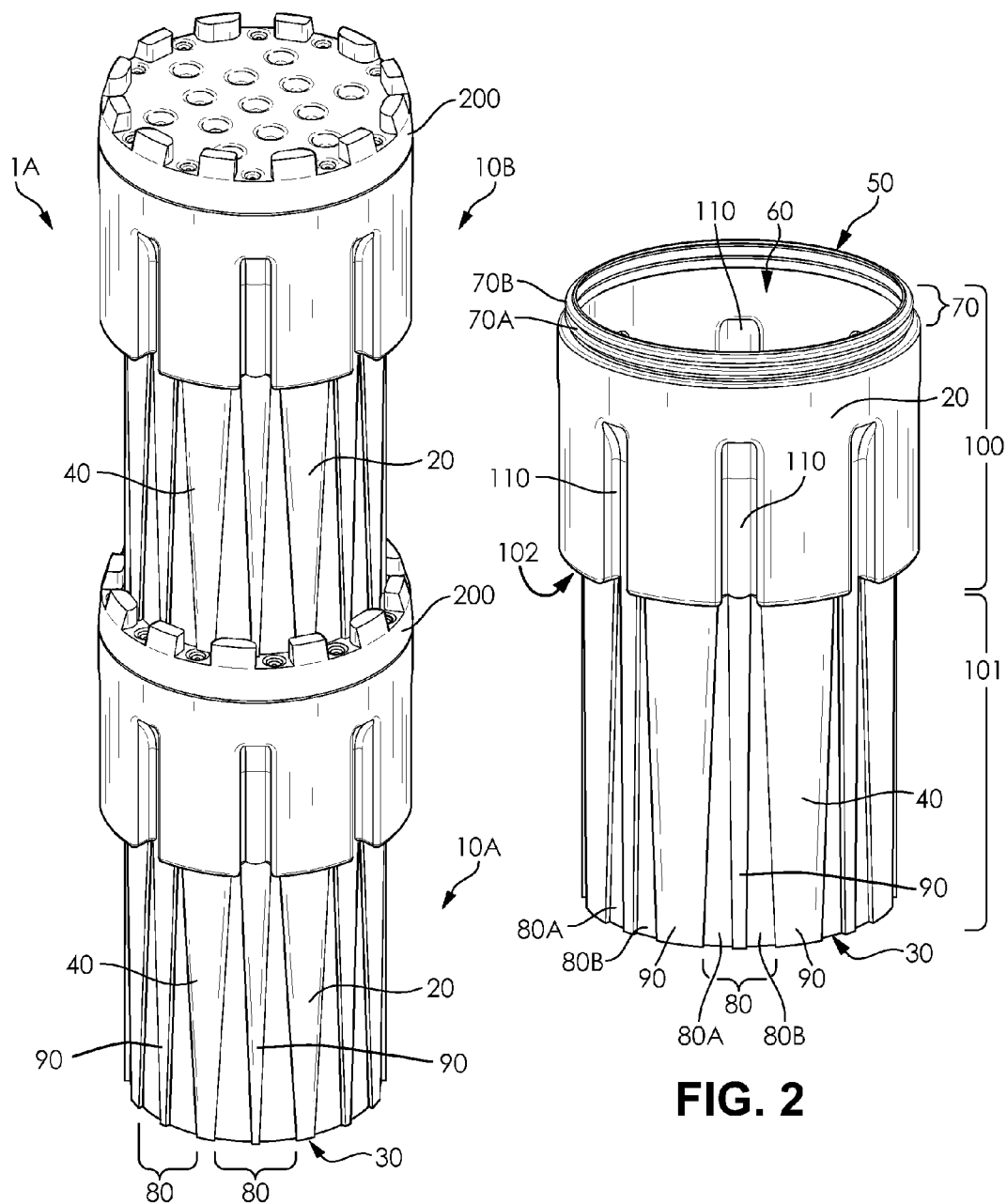
FIG. 1 is a perspective view showing two overpack salvage drums in a stacked arrangement in accordance with the present subject matter.
FIG. 2 is a perspective view of a drum body of an overpack salvage drum in accordance with the present subject matter.

The present subject matter is directed toward an overpack salvage drum as will be described in more detail with reference to FIGS. 1-10, and to related methods. The overpack salvage drum 10 is adapted to receive and contain an associated package. The overpack salvage drum 10 includes a drum body 20 and a lid 200. The lid 200 is selectively engageable to the drum body 20 to close or open the overpack salvage drum 10 as desired.

In several embodiments, the drum body 20 and lid 200 comprise a durable, chemical resistant polymer such as, for example, linear low density polyethylene (LLDPE), or medium density polyethylene (MDPE). However, it will be appreciated that other suitable polymers or other materials can be used, if desired. The drum body 20 and the lid 200 can be formed by rotational molding or other polymer molding process.

Drum Body

In several embodiments, the drum body 20 comprises a single-walled structure including a bottom wall 30, a side wall 40, and an open top 50. The bottom wall 30 and side wall 40 cooperate to define an interior volume 60 of the drum body 20, which can receive a package (e.g., a damaged or leaking container) to be overpacked. The lid 200 is configured to selectively engage the drum body 20, e.g. by screwing on to drum body, for selectively closing the open top 50 of the drum body 20 to thereby contain an associated package.

The exterior surface of the bottom wall 30 may be substantially planar and optionally smooth, or may include surface features if desired, for example those disclosed in U.S. Pat. No. 8,281,948 to Stanek, et al., which is incorporated herein by reference. In other embodiments, the bottom wall 30 of the drum body 20 may comprise a textured exterior surface.

The side wall 40 of the drum body 20 comprises an upper side wall portion 100, a lower side wall portion 101, and one or more male (i.e. protruding) drum threads 70 for engaging corresponding female threads 250 on the lid 200. In several embodiments, the upper side wall portion 100 of the drum body 20 has a larger diameter than the lower side wall portion 101 of the drum body 20 as shown in particular in FIGS. 1-2, and 10.

In several embodiments, an inside diameter of the upper side wall portion 100 of drum body 20 is greater than an outside diameter of the lower side wall portion 101 of the drum body 20. As will be understood, this configuration allows a lower side wall portion 101 of a first drum body to be received within (i.e. nested in) an upper side wall portion 100 and within a lower side wall portion 101 of a second drum body, and in an interior 60 of the second drum body. In this way, several drum bodies can be nested together, one inside another, in a stacked arrangement, which minimizes shipping space and storage space occupied by multiple drum bodies.

As shown in FIG. 2, the drum body 20 includes a plurality of upper side wall recesses 110, each defining a concave indentation extending inward from an outer surface of the upper side wall portion 100. The upper side wall recess 110 correspondingly defines a convex protrusion extending inward from the inner surface of the upper side wall portion 100 and into the interior space 60 of the drum body 20. In several embodiments, the upper side wall recesses 110 may not extend the full height of the upper side wall portion 100, which allows the drum body 20 to flex during an impact to the drum body 20.

When several drum bodies are stacked together, nested one inside another, the concave recess defined by the upper side wall recess 110 extending in from an outer surface of the upper side wall portion 100 of an inner nested drum body, can align and fit over the convex protrusion defined by the upper side wall recess 110 extending into the interior 60 from the inner surface of the upper side wall 100 of an outer nested drum body. This mating between a concave recess on one drum body with a convex protrusion on another drum body, serves as a self-centering feature when two or more drum bodies 20 are nested together in a stack prior to use.

The upper side wall recesses 110 can also be used to hold or secure the drum body 20 when the lid 200 is being sealed thereto.

The drum body 20 also includes a shoulder 102 comprising the transition between the upper side wall portion 100 and the lower side wall portion 101 as shown. The shoulder 102 can be used to lift a drum body 20, a stack of drum bodies, or a filled overpack salvage drum (10A or 10B), e.g., via the use of the forks of a lift truck.

The male drum threads 70 are situated on an exterior circumferential surface of the upper side wall portion 100 proximate to the open top 50 of the drum body 20. It will be appreciated that the height, pitch and width of the threads 70 can be determined in view of the size of the overpack salvage drum 10. In one embodiment, the threads 70 allow the lid 200 to rotate about 180° from a starting position to a fully seated/sealed position.

It will be appreciated that the drum body 20 could be provided with multiple threads, i.e. "multiple-start" threads. Use of multiple-start threads allows for a better and stronger seal between the drum body 20 and the lid 200 and offers better performance in all of the required USDOT and UN tests, including drop tests and pressure tests, wherein when the drum is pressurized, the lid moves less to the side compared to single start threads. The multiple-start threads more evenly distribute the stretch of the threads during the pressure test helping to retain a more constant seal between the lid to the drum body, as well as helping to more evenly distribute the stacking load applied to the sealed overpack salvage drum resulting from the load applied to the circular cavity 380 on the top side 201 of the lid 200. The multiple-start threads offer stronger seals while occupying less height when compared to the space required for single-start threads of comparable seal strength. Therefore, multiple threads offer significant height savings in the drum body (and lid) as compared to conventional single-thread overpack salvage drums of similar sealing strength.

In accordance with the present subject matter, the drum body 20 and lid 200 can be provided with (n) threads, where n≥2 and n≤5. In one aspect, two independent male threads 70A, 70B are used on the drum body 20. The protruding threads 70A, 70B may have starts separated by about 180° from each other about the circumference of the drum body 20.

The lower side wall 101 the drum body 20 includes a plurality of lower side wall recesses 80 extending into lower side wall land areas 90. The recesses 80 offer stability and strength to the lower side wall portion 101 of the drum body 20. As shown in FIGS. 1-2, the lower side wall recesses 80 have a length that extends substantially vertically from the bottom wall 30 toward the upper side wall portion 100, and taper to a smaller size as they extend upward from the bottom wall 30. This tapering configuration along a length of the lower side wall recesses 80 allow the drum body 20 to flex during an impact.

The lower side wall recesses 80, along with the upper side wall recesses 110, inhibit the formation of a vacuum between stacked and nested drum bodies and thus make it easier to separate a drum body 20 from a stack of drum bodies.

Lid

The overpack salvage drum 10 includes a lid 200 for closing or sealing the open top 50 of the drum body 20 to thereby contain an associated package in the interior 60 of the overpack salvage drum 10. The lid 200 can comprise a double-walled structure (FIG. 4-5) including a top side 201 and a bottom side 202.

The lid 200 can include an annular skirt portion 330 (see FIGS. 4, 5 and 7-9) extending downwardly from the perimeter of a top side 201 of the lid 200. The annular skirt 330 terminates to define a circumferential bottom peripheral edge 350.

Figure 5:
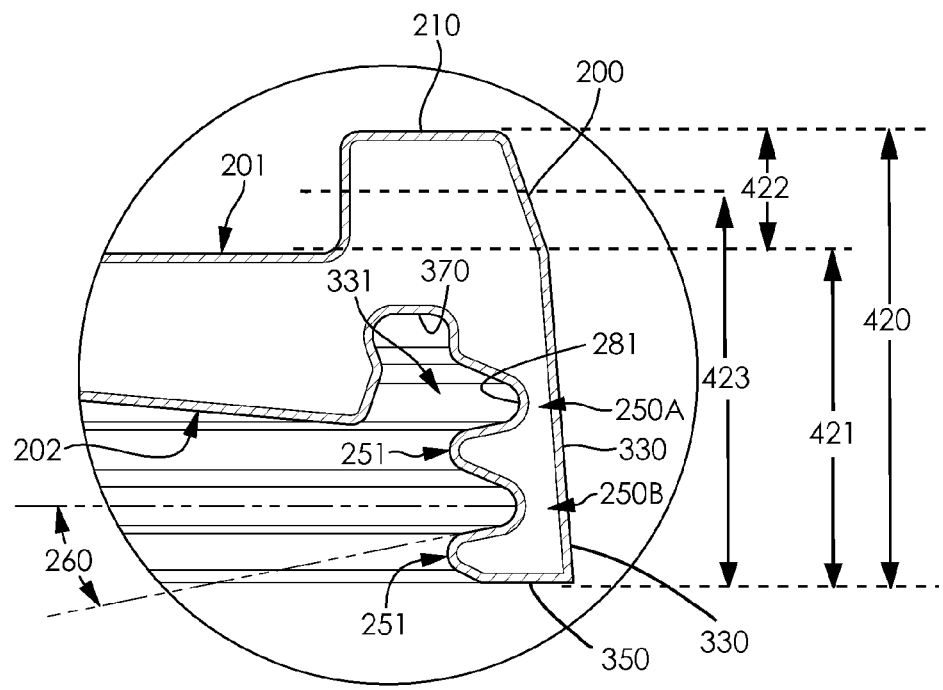
FIG. 5 is a detailed cross-sectional view of the lid of FIG. 4 located within circle 5.

In one embodiment and with reference to FIG. 5, the lid 200 includes an annular groove 370 formed in the bottom side 202 of the lid 200. The annular groove 370 extends completely around the lid 200 adjacent to the skirt 330. The annular groove 370 is adapted to receive a sealing material, e.g. a gasket, which may be received within the annular groove 370 before the lid 200 is engaged with the drum body 20. The gasket is adapted to be sealingly compressed between an upper edge of the drum body 20 and the annular groove 370 when the lid 200 is threadingly engaged with the drum body 20.

In accordance with the present subject matter, one or more female (i.e. recessed) threads 250 is formed on an inside circumferential surface 331 of the annular skirt portion 330. The recessed female lid threads 250 are adapted to threadingly engage (i.e., receive) the one or more raised male drum threads 70 formed on the exterior circumferential surface of the upper side wall portion 100 of the drum body 20. The male drum threads 70 have a complimentary fitting shape to the shape of the recessed female lid threads 250.

In one embodiment, the female threads 250 have a modified ACME thread design, featuring a half thread angle 260 on the mating surface of about 11° as measured from horizontal, and a full thread angle (i.e. double of thread angle 260) of about 20°-22°. In one aspect, the mating surfaces of the female threads 250 on the lid 200 and the male threads 70 on the drum body 20, are both about 11°, while the full thread angle of the female threads on the lid are about 20° and the full thread angle of the male threads on the drum body are about 22°. These thread angles allow better material flow while molding the threads, yet eliminate issues relating to mating threads slipping off each other on a sealed overpack salvage drum. The female threads 250 can have rounded thread crests 251 with a continuous radius of curvature of about 0.25 inches for example, or larger or smaller as desired. The thread root 281 can include a flat central portion and curved edges on each side of the flat central portion. The curved edges of the thread root 281 can have a radius of curvature that is smaller than the radius of curvature of the thread crest 251, for example a radius of curvature of about 0.188 inches. It will be appreciated that lid threads 250 can comprise different dimensions and arrangements if desired, and that the disclosed dimensions are not per se critical.

The lid 200 may be selectively engaged to the drum body 20 using threads 250 on the lid 200 and the corresponding threads 70 on the drum body 20, which have a complimentary fitting shape configured to mate with each other. The threads 250 on the lid 200 and the threads 70 on the drum body 20 may each comprise one (i.e. single-start thread) or more threads (i.e. multiple-start threads). In one aspect, the lid 200 includes at least two independent lid threads 250A, 250B (FIG. 5) for engaging/mating with at least two corresponding independent drum threads 70A, 70B (FIG. 2) provided on the drum body 20.

Such a multiple-start threading engagement between the lid and the drum body is stronger than a single-start threading engagement. Therefore, male threads 70A, 70B can be configured to be shorter in length, and thus occupy less vertical space on the upper side wall portion 100 of the drum body than would be required for a single-start thread of comparable strength. Similarly, female lid threads 250A, 250B can be configured to occupy less vertical space on skirt portion 330 of the lid 200 than would be required for a single-start thread of comparable strength.

As such, the multiple-start threads 70A, 70B and 250A, 250B occupy less vertical space on the drum body 20 and the lid 200, respectively, than single-start threading engagements offering comparable sealing strength. In this way, stacks of drum bodies and lids take up less vertical space than stacks of conventional drum bodies and lids.

The use of at least one raised thread 70 on the exterior surface of the drum body 20 and at least one recessed thread 250 on the inside circumferential surface 331 of the skirt 330 of the lid 200 may be advantageous because in the event that pressure were to build up within the interior 60 of drum body 20, such a thread configuration could tend to tighten the connection between the lid 200 and the drum body 20. However, the opposite arrangement could be used, if desired. It will be appreciated that the number, pitch, depth and width of female lid threads 250 will correspond to the number, pitch, depth and width of the male drum thread 70.

Figure 7:
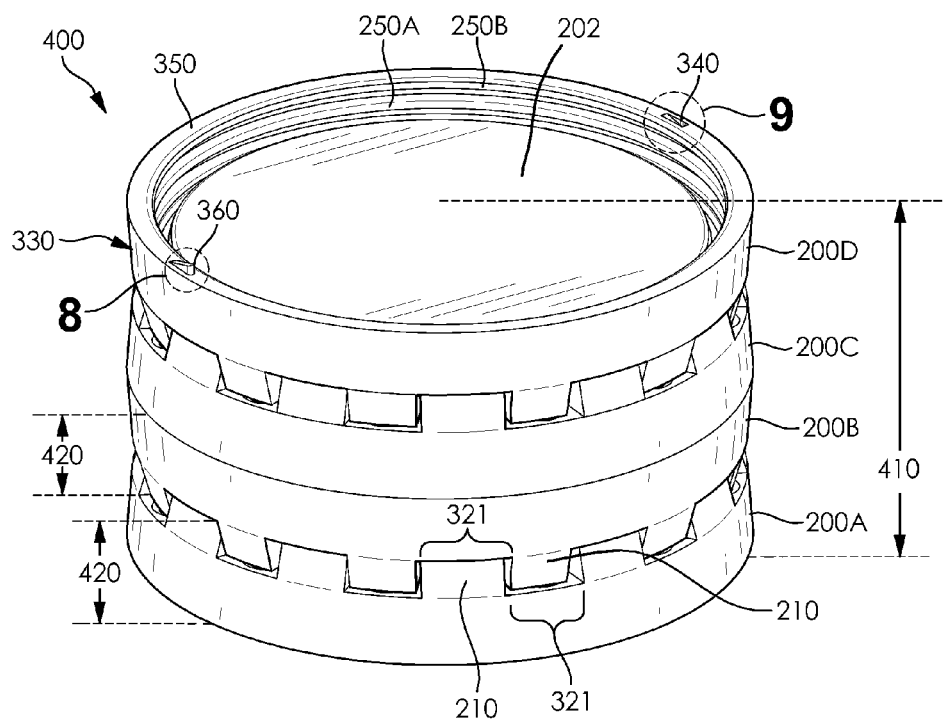
FIG. 7 is a perspective view of four lids in a stacked configuration in accordance with the present subject matter.
Figure 8:
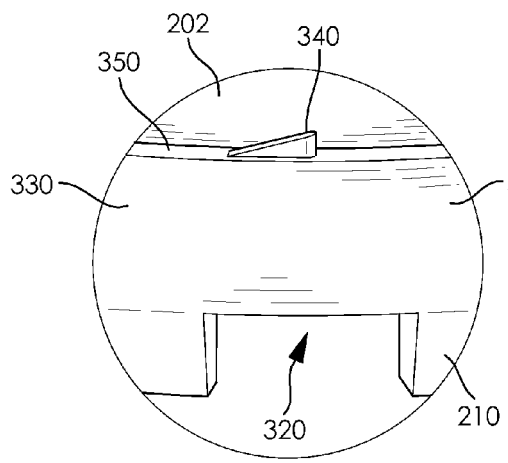
FIG. 8 is a detailed perspective view of the lid of FIG. 7 located within circle 8.
Figure 9:
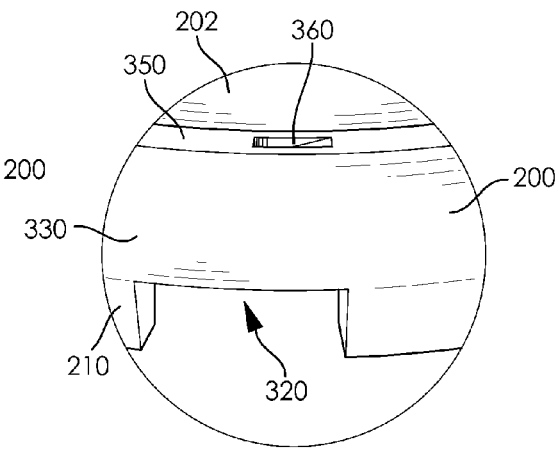
FIG. 9 is a detailed perspective view of the lid of FIG. 7 located within circle 9.

In another embodiment as shown in FIGS. 7-9, the lid 200 includes one or more lugs 340 extending/protruding downward from the bottom peripheral edge 350 and one or more corresponding lug recesses 360 penetrating into the bottom peripheral edge 350. When two lids, for example lids 200B and 200C in FIG. 7, are stacked one upon another such that the bottom peripheral edges 350 of the two lids are facing, the lugs 340 of one lid are configured to fit inside the lug recesses 360 of the other lid. Such mating of the bottom peripheral edges 350 of two lids 200B, 200C inhibits the lids 200B, 200C from sliding horizontally relative to each other.

In another aspect, a bottom peripheral edge 350 of the lid 200 includes a ring, or portions thereof extending/protruding downward from the bottom peripheral edge 350. When two lids are stacked one upon another such that the bottom peripheral edges of the two lids are facing, the ring, or portions thereof protruding from the bottom peripheral edge of one lid is configured to mate in an interlocking manner with the ring, or portions thereof extending from the bottom peripheral edge of the other lid.

The rings on the two lids can interlock, for example wherein a protruding ring having a smaller diameter on one lid fits inside a ring having a larger diameter on the other lid, or vice versa. This configuration would require that there be two different types of lids, each type including one protruding ring with either the smaller or larger diameter.

Alternatively, there could be one type of lid including a portion of a larger diameter ring and a portion of a smaller diameter ring protruding downward from the bottom peripheral edge 350. The ring portions with the smaller and larger diameters can be alternately positioned around the bottom peripheral edge of the lid. In this embodiment, the smaller diameter ring portions on a first lid can fit inside the larger diameter ring portions on a second lid. In this way, there is only a need to produce a single type of lid having interlocking ring portions on a bottom peripheral edge.

As with the lugs and lug recesses, such mating of the rings, or portions thereof that extend from a bottom peripheral edge of the two lids allows the lids to be braced relative to each other by inhibiting the lids from sliding horizontally relative to each other.

In accordance with the present subject matter, the lid 200 also includes a plurality of castellations 210 projecting upwardly from the top side 201 of the lid 200 and circumferentially arranged around a periphery of the top side 201 of the lid 200. The plurality of castellations 210 are separated from each other by gaps 320. The castellations 210 perform a variety of functions as is explained in more detail herein, including facilitating the compact stacking of lids together (see FIG. 7), horizontally securing stacked lids so as to improve safety, and also allowing for the use of beams of different size and multiple beams to aid in securing or removing the lid to the drum body.

In the several figures, the castellations 210 are each shown to have a general cuboid shape. However, it will be understood that the size and shape of the castellations 210 is not particularly limited by the present subject matter, and the present subject matter includes castellations 210 each having any shape or size suitable for performing the variety of functions explained elsewhere herein. For example, the castellations can each have a general shape comprising a sphere, a cylinder, a cone, a polyhedron, an ellipsoid, a torus, a polygon, or a combination thereof.

Figure 3:
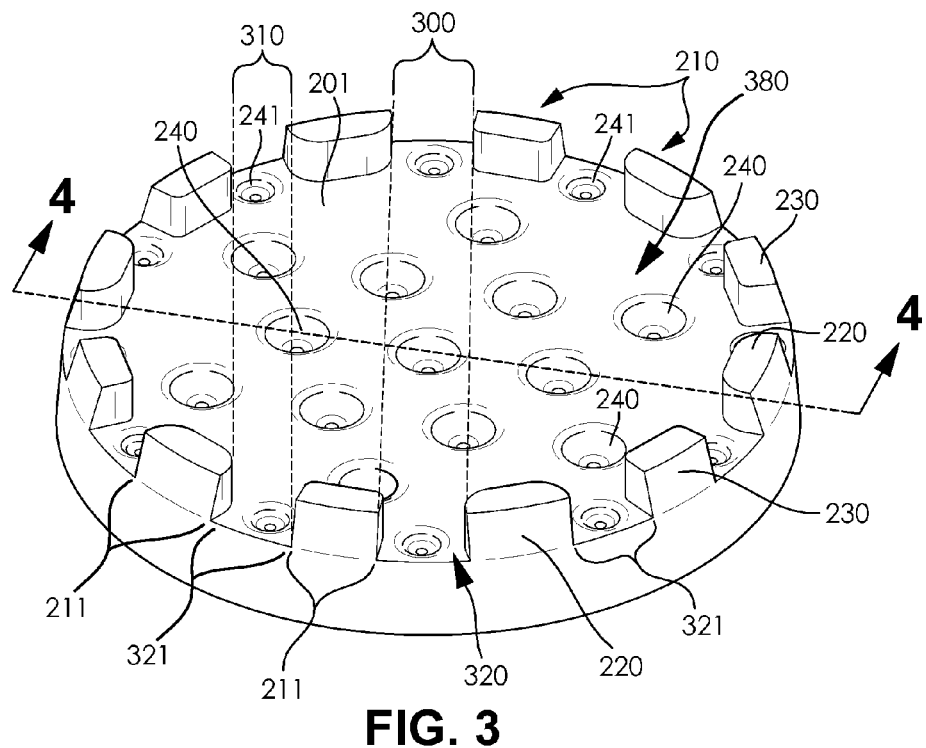
FIG. 3 is a perspective view of a lid of an overpack salvage drum in accordance with the present subject matter.

The castellations 210 may be equally spaced apart around a periphery of the top side 201 of the lid 200, as shown in FIG. 3, to define a plurality of gaps 320 between castellations 210. In several embodiments, the gaps 320 have a circumferential size 321 that is larger than a circumferential dimension 211 (i.e. width) of the castellations 210. That is, when the top side 201 of the lid 200 is viewed in plan, the gaps 320 separating the plurality of castellations 210 have a larger circumferential dimension 211 than the circumferential dimension 211 of the castellations 210. In other words, the distance between adjacent castellations (which may be defined by the circumferential size 321 of the gaps 320) is greater than the distance between adjacent gaps (which may be defined by the circumferential dimension 211 of the castellations 210).

In several embodiments, the lid includes a plurality of different types of castellations. In one aspect as specifically shown in FIGS. 3 and 6, the lid 200 includes two types of castellations 220, 230, wherein one type of castellations 220 has an arcuate inner facing side 221 (i.e. inner face) and the other type of castellations 230 has a flat inner facing side 231. The two types of castellations 220, 230 are arranged in an alternating fashion around a periphery of the top side 201 of the lid 200.

The size and shape of the two types of castellations 220, 230 and their respective inner faces 221, 231 are not particularly limited by the present subject matter. In several embodiments, the castellations 220 extend farther in toward the center of the lid 200 as compared to castellations 230. This configuration can be seen in FIG. 6, wherein castellations 220 mate with recesses 80A of an upper overpack salvage drum 10B, while castellations 230 do not contact the upper overpack salvage drum 10B. This configuration can be varied for example, wherein castellations 230 can be designed to contact the land area 90 of the lower side wall 101 of the upper overpack salvage drum 10B when castellations 220 mate with the lower side wall recesses 80.

The number of castellations 210, the circumferential dimension 211 (i.e. width) of the castellations 210, and the circumferential size 321 or the gaps 320 between the castellations 210 is also not particularly limited by the present subject matter, so long as the castellations 210 on one lid can interlock/interdigitate with castellations 210 on another lid when the two lids are stacked with castellations on each lid facing each other.

In one embodiment, the double-walled lid 200 is provided with a plurality of "kiss off" portions 240 for providing strength and rigidity to the lid 200. In one aspect, the kiss offs 240 project downwardly in a hemispherical manner from the top side 201 toward the bottom side 202 of the lid 200. The kiss off portions 240 can be arranged in any desired configuration across the top side 201 of the lid 200 and may comprise other shapes, such as rectangular or square. For example, the kiss off portions 240 may be formed where the two spaced-apart walls (i.e. top side 201 and bottom side 202) of the double-walled lid 200 are brought or formed together to thereby contact at discrete locations (see FIG. 4). It will be appreciated that the number and location of kiss off portions 240 will be dependent upon the dimensions of the overpack salvage drum 10, which is dependent upon the dimensions of the package to be overpacked. It will also be appreciated that the kiss offs 240 can be formed in any desirable shape or pattern on the top side 201 of the lid 200.

Figure 4:
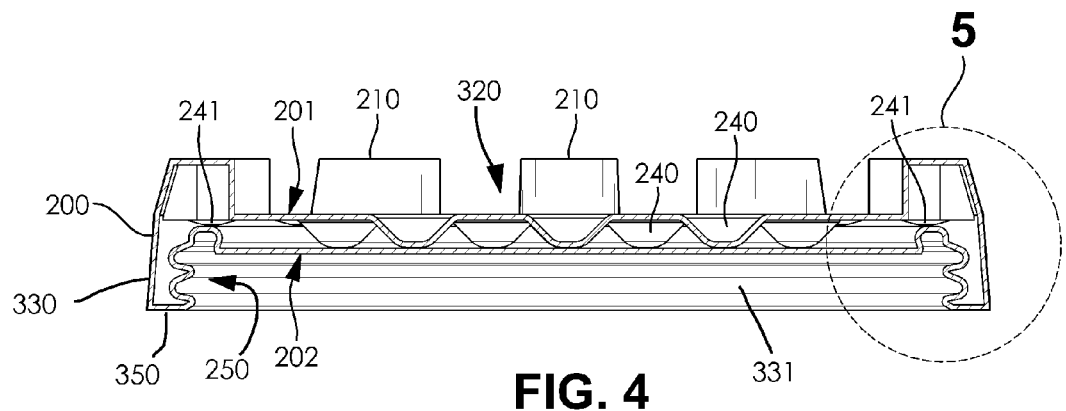
FIG. 4 is a cross-sectional view of the lid of FIG. 3 taken along line 4-4.

The lid 200 may also include a plurality of additional kiss-off portions 241 provided between the castellations 210, 220, 230, as provided in FIGS. 1 and 3-4, for providing additional strength to the lid 200 in the gaps 320 between castellations 210, 220, 230. The kiss offs 241 may be produced in the same way and in the same shape as kiss offs 240, or may be varied therefrom. In one embodiment as shown in FIGS. 1 and 3-4, kiss offs 241 in gaps 320 between castellations are smaller in size (depth and/or diameter) than those kiss-offs 240 (which can also be varied in size) on the remainder of the lid 200 and which are not situated between castellations 210, 220, 230.

The castellations 210 on the lid 200 may define various channels (e.g. channels 300, 310 shown in FIG. 3) having different widths, which extend in a straight path laterally across the top side 201 of the lid 200, from a gap 320 between a first pair of adjacent castellations, to a gap 320 between a second pair of adjacent castellations that are remote from the first pair of castellations. In one embodiment, the channels are unobstructed—that is, no structure or impedance is located in the channels—so as to allow a wide variety of beams, bars, or other elongated objects to be inserted in the channels and used as a lever to push against the castellations 210 in order to provide torque for assisting with rotationally moving (i.e. tightening or loosening) the lid 200 in relation to the drum body 20. The beam(s) can be inserted in channels 300, 310 among others.

As shown in FIG. 3, a larger channel 300 extends directly across the diameter of the lid 200 between gaps 320 that are directly opposite from each other on the periphery of the lid. A smaller channel 310, which is not as wide as the larger channel 300, extends across the lid 200 between gaps 320 that are not directly opposite from each other on the periphery of the lid. It will be appreciated that depending on the size and number of castellations, the lid may define various channels other than channels 300, 310. As can be seen, the two channels 300, 310 have different widths and do not intersect each other.

The larger channel 300 may be sized to accept the broad dimension of a conventional 2×4 wood beam, or other beam made of different material and of similar size, and can be approximately 3.82 inches wide. The smaller channel 310 may be sized to accept the smaller dimension of a conventional 2×4 wood beam, or other beam made of different material and of similar size, and can be approximately 1.64 inches wide. As will be appreciated, the positioning of the castellations as shown in FIG. 3 allows for using beams of different dimension and even allows for using multiple beams at the same time (e.g., from two sides) in order to rotationally move the lid 200 in relation to the drum body 20.

Figure 6:
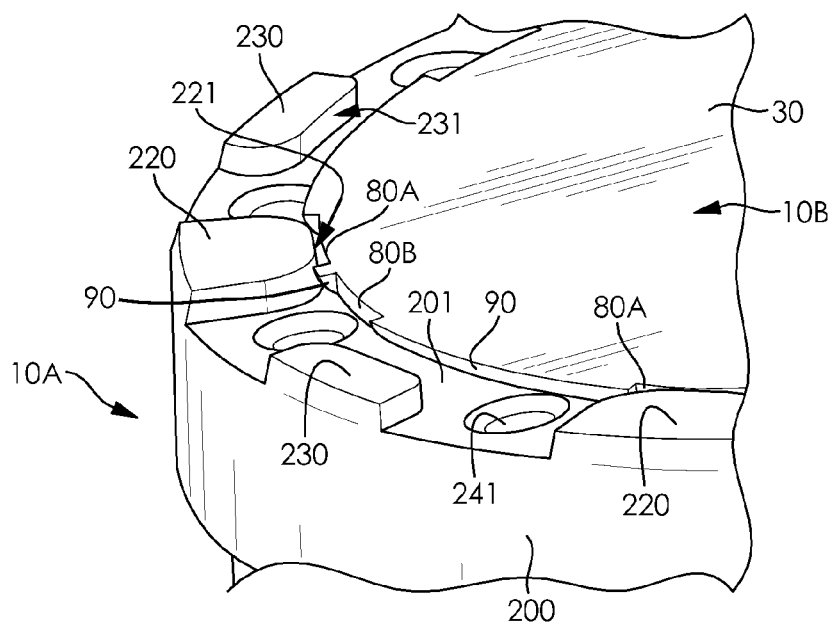
FIG. 6 is a detailed perspective view of FIG. 1 showing a section taken through the bottom portion of the uppermost drum.

To facilitate stacking of two or more sealed overpack salvage drums 10 as configured in FIG. 1, the top side 201 of the lid 200 and the castellations 210 may together define a circular cavity 380 (FIG. 3) configured to receiving a bottom wall 30 of a drum body 20 as shown in FIGS. 1 and 6.

In FIG. 6, it is shown in detail that the bottom wall 30 of a drum body of a top/upper overpack salvage drum 10B contacts the top side 201 of a lid 200 of a bottom overpack salvage drum 10A and between the castellations 220, 230 of the bottom drum. As can be seen, the castellations 220 with the arcuate inner face 221 of the bottom drum are configured to be mated with lower side wall recesses 80 in the drum body 20 of the upper drum. This mating between castellations 220 and recesses 80 may include a portion of the castellations 200 sitting within the lower side wall recesses 80, or may include the arcuate inner face 221 of castellations 220 contacting the surface of the lower side wall recesses 80.

In one aspect, the overpack salvage drum 10 is configured such that the bottom wall 30 of the an upper drum body 20 is unable to contact the top side 201 of the lower lid 200, unless the castellations 220 of the lower lid 200 are mating with the recesses 80 of the upper drum body 20, and vice versa. In this way, a drum body 20 can not be properly seated on the top side 201 of a lid 200 without the drum body 20 being rotationally secured in relation to the lid 200.

In one embodiment, wherein the bottom wall 30 of a drum body 20 is brought into contact with the top side of a lid 200 and the first type of castellations 220 are received in the plurality of recesses 80 in the side wall 40 of the drum body 20, thereby substantially vertically centering the drum body 20 in relation to the lid 200 (as shown in FIGS. 1 and 6, for example) in circular cavity 380, then the castellations 230 comprising a flat inner face 231 are spaced from (i.e. do not contact) the drum body 20. In one aspect of this embodiment, castellations 220 contact the recesses 80 of the drum body 200.

As shown in FIG. 6, the castellations 220 are mated with recesses 80A. However, it will be appreciated that the castellations 220 can be mated with recesses 80B. In either event, the mating of castellations 200 with recesses 80A or 80B acts to rotationally lock/secure the upper drum body in relation to the lower lid when two or more salvage drums are in a stacked arrangement 1A as shown in FIG. 1.

In this stack 1A of sealed (optionally containing a package) overpack salvage drums, the bottom wall 30 of the drum body of the upper overpack salvage drum 10B is resting on the top side 201 of the lid 200 of the bottom overpack salvage drum 10A. The plurality of lower side wall recesses 80 are adapted to align and mate with the castellations 220 having the arcuate inner facing side 221 of the lid 200 of the bottom overpack salvage drum 10A.

The mating between the castellations 220 and recesses 80A forms an interlocking engagement between the two stacked overpack salvage drums 10A, 10B, which reduces sliding and displacement of the two drums relative to each other. The cooperative engagement between the castellations 220 having an arcuate inner facing side 221 and the recesses 80A also ensures that the upper overpack salvage drum 10B is vertically centered with respect to the lower overpack salvage drum 10A on the lid 200 thereof as shown in FIG. 1. Such vertical alignment of the two overpack salvage drums provides an additional safety feature by preventing a stack 1A of overpack salvage drums from leaning (due to offset stacking, for example) and thus becoming unstable to a point of tipping over.

Because the lid 200 is a double-walled construction, and because the lid 200 includes the kiss-off portions 240, 241, the lid 200 is sufficiently strong enough to accommodate the weight of a plurality of sealed, filled overpack salvage drums 10 stacked one on top of the other.

Figure 10:
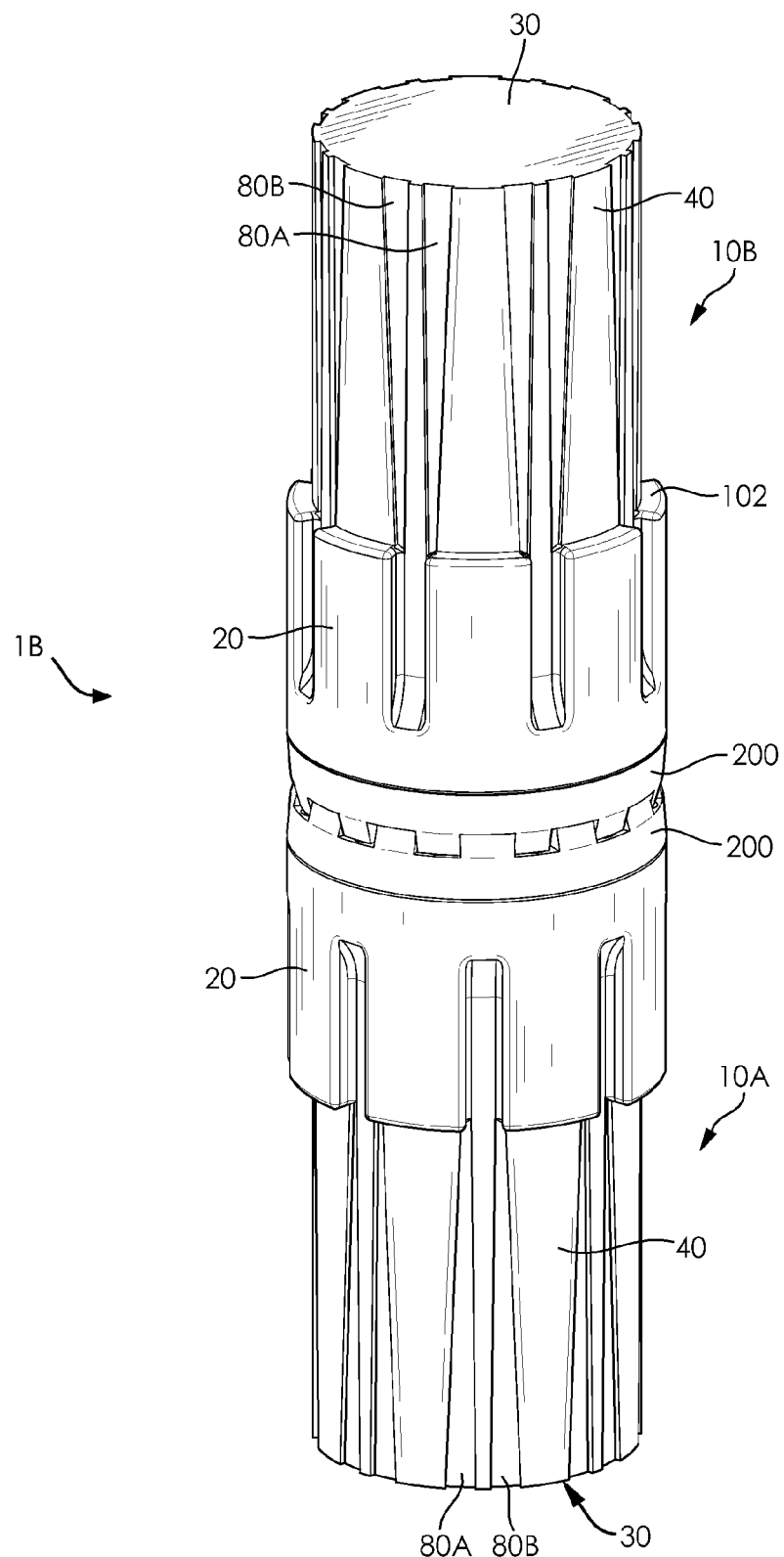
FIG. 10 is a perspective view showing two overpack salvage drums in a stacked arrangement in accordance with the present subject matter.

In an alternate embodiment shown in FIG. 10, a stacked assembly 1B includes a first sealed overpack salvage drum 10A stacked lid-to-lid with a second sealed overpack salvage drum 10B. In other words, the second overpack salvage drum 10B is upside down and rests on top of the first overpack salvage drum 10A, such that the lids 200 of the two drums are in contact. In this configuration, the top side of first lid of the first overpack salvage drum 10A is facing the top side of the lid of the second overpack salvage drum 10B. The castellations on each lid interdigitate with castellations on the other lid, such that castellations on the lid of the first overpack salvage drum 10A fit in the gaps between the castellations on the lid of the second overpack salvage drum 10B, and vice versa. This stacking arrangement 1B may offer added safety during shipping or storage of stacked drums compared to an arrangement where both drums are right side up because the castellations on the two lids are interlocking. This stacked configuration 1B of overpack salvage drums 10A and 10B may be acceptable under certain conditions, for example when a package in overpack salvage drum 10B is under the maximum rated capacity of the overpack salvage drum by a certain percentage.

The configuration of this stack 1B of overpack salvage drums would also allow a user to tighten both overpack salvage drums 10A and 10B at the same time if desired. The first (i.e. bottom) drum 10A could be held stationary as the second (i.e. top) drum body was turned to tighten it down into the associated top lid. Continued rotation of the second drum body would eventually cause the first (i.e. bottom) lid to tighten on the first overpack salvage drum 10A. This process would result in tightening two drums at once by rotating only the top drum body 20 of the second overpack salvage drum 10B.

In either embodiment for the stacked assembly of overpack salvage drums, the stacked assembly of drums 1A or 1B may be Pipeline and Hazardous Material Safety Administration (PHMSA) approved.

The lids 200 are also configured to stack with one another as shown in FIG. 7, which shows four lids 200A-200D stacked one atop another in a vertically compact arrangement defining a lid stack 400. The lids 200A-200D are stacked in an alternating lid orientation, wherein the top side 201 of one lid is facing up, and the top side of the next lid is facing down. For example, the top side of the bottom lid 200A is shown to be facing upwardly, and could be secured to a drum body. The second lid 200B from the bottom has an alternated lid orientation, wherein the top side of the second lid 200B is facing downwardly. In this orientation, the castellations 210 of the second lid 200B are received in the gaps 320 between the castellations 210 of the bottom lid 200A, and vice versa. As is shown, the alternating lid orientation is continued with the next two lids 200C, 200D.

The castellations 210 on one lid are all arranged at angles to one another around the periphery of the lid 200, wherein the inner faces (221 or 231) of the castellations are all facing radially in toward the center of the lid 200. The angle of the castellations relative to one another, and the positioning of the gaps 320 in which the castellations sit, thereby prevents sideways/horizontal separation of the two lids when stacked, thus providing an added safety feature for the lid stack 400 not available in conventional salvage drum lids.

More specifically, when two or more lids are stacked one on top of the other with castellations facing each other such as for storage or transportation of the lids, as shown for example in FIG. 7 between lids 200A and 200B, the castellations 210 on the lids are configured to interdigitate with each other. For example, when two lids 200A, 200B are stacked one upon the other as shown in FIG. 7 so that top sides 201 of each lid are facing, the castellations 210 of one lid 200A can fit in the gaps 320 of the other lid 200B, and vice versa. Additional lids 200C, 200D can be stacked in a similar manner.

In this way, a height 410 of a lid stack 400, including two or more lids of the present subject matter, will not equal the total of the individual lid heights 420 (i.e. the distance from bottom peripheral edge 350 to top of castellations 210) added together as is conventional, but will be less than that total height due to the space saved by the interlocking castellations. For example as shown in FIG. 7, the height 410 of a lid stack 400 will equal the total of the added individual heights 421 (FIG. 5) between the bottom peripheral edge 350 and the top side 201 of each lid in the stack 400, along with half the total of the added heights 422 between the top side 201 of the lid 200 and the top of the castellations 210 of each lid in the stack 400. Only half the total of the added heights 422 of each lid in the stack 400 will be included in the total height 410 of the lid stack 400, because these heights 422 are overlapping between lids 200A, 200B and 200C, 200D. In other words, each lid 200 has a stacking height 423 (see FIG. 5) that is the distance from the bottom peripheral edge 350, to a point approximately half way between the top side 201 of the lid and the top of the castellations 210.

The height 410 of a lid stack 400 including two or more lids of the present subject matter stacked with castellations facing, will be the sum total of the stacking heights 423 of the lids, which is less than the height of a comparable stack of conventional salvage drum lids having the same lid height 420 as measured from a bottom peripheral edge to a top of the castellations. This is because conventional salvage drum lids do not have interlocking castellations and therefore do not define stacking heights 423 that are less than the overall lid height 420. As such, the overall height of the conventional lid stack is simply the total of the individual lid heights 420 added together. For instance, when two conventional lids are stacked one upon another with castellations facing each other, the castellations do not interdigitate. As such, the total height of a conventional lid stack will simply be the combined height 420 of the individual lids.

In FIG. 7, the third lid 200C from the bottom is stacked on the second lid 200B from the bottom such that the bottom peripheral edge 350 of each lid 200B, 200C is facing. In one embodiment, the lids 200A-200D are all identical, and feature a lug 340 and also a lug recess 360 provided on the bottom peripheral edge 350. This feature is shown on lid 200D, wherein one lug 340 and one lug recess 360 are provided on opposite sides of the bottom peripheral edge 350, although this configuration is not required.

Furthermore, the lug 340 and the lug recess 360 have complimentary fitting shapes, wherein the lug 340 has a shape or surface contour that is complimentary to the shape or surface contour of the lug recess 360 so that the lug 340 from one lid can mate with the lug recess 360 on another lid by fitting inside the lug recess 360 of the other lid. In FIGS. 7-9, the lugs 340 are shown to have a general shape comprising a triangular prism and the lug recesses 360 are shown to have a general shape comprising a recessed shape complimentary to the shape of the lugs 340, which are configured to internally receive the lugs 340. However, it will be understood that the size and shape of the lugs and lug recesses are not particularly limited by the present subject matter, and the present subject matter includes lugs and lug recesses having any shape or size suitable for performing the variety of functions explained elsewhere herein. For example, the lugs can have a general shape comprising a sphere, a cylinder, a cone, a polyhedron, an ellipsoid, a torus, a polygon, or a combination thereof; and the lug recesses can have a complimentary shape to the lugs so as to internally receive the lugs.

In this way, the lids 200B, 200C can be oriented such that a lug 340 from one lid is received internally within a lug recess 360 of the other lid, and vice versa. Multiple lugs 340 and lug recesses 360 can be utilized, if desired, provided they are oriented and spaced in a manner so that they align with each other when two lids are stacked with bottom peripheral edges 350 facing each other, for example as shown in FIG. 7 between lids 200B, 200C.

The lugs and recesses, or rings, as well as the castellations, prevent the lids from sliding horizontally off each other when stacked one atop another. As such, the lids can be conveniently and safely stacked one upon another as shown in FIG. 7, while the interlocking castellations also reduce the height 410 of the lid stack 400. Such arrangement allows for compact stacking of the lids for storage or shipment. Furthermore, this configuration allows for the compact shipping and storage of overpack salvage drums, as compared to current space requirements. More compact storage is achieved by the arrangement of the castellations 210 and gaps 320 on the lids 200, the engagement of the bottom peripheral edges 350 of the lids 20, and the use of multiple threads 70A, 70B and 250A, 250B, which makes the lid height 420 less than would be necessary for the same seal strength if a single thread was used.

The overpack salvage drums 10 can therefore be stacked in a manner that takes up less space than occupied by a stack of conventional overpack salvage drums having the same capacity. A comparison between the present subject matter overpack salvage drums and conventional overpack salvage drums was made, and the comparison showed that four drum bodies 20 and four lids 200 in accordance with the present subject matter can be stacked in less vertical space (and the same horizontal space) than four conventional drum bodies and three conventional lids.

The savings in height for the present lid stack 400 is due, in part, to the efficient double thread design (including for example, threads 250A, 250B) and, in part, to the interlocking engagement of the castellations 210 on the lids 200.

The savings in height for a stack of drum bodies 20 is due to the efficient double thread design of threads 70A, 70B. According to an alternative embodiment of the present subject matter, wherein a height of the upper side wall portion 100 is minimized, it has been shown that for a 95 gallon overpack salvage drum, the height of the upper side wall portion 100 could be reduced by about six inches, to about 10.25 inches, compared to conventional overpack salvage drums. In this embodiment, it has been found that when five complete overpack salvage drums 10, including five lids 200 and five drum bodies 20, of this alternative configuration are stacked, the five alternative overpack salvage drums 10 can fit in the same vertical space as occupied by four conventional drum bodies and three conventional lids having 95 gallon capacity. This space saving can be achieved while also obtaining the added safety and performance features described above.

As a result of these features, the overall height of a stack of the present overpack salvage drums can be about 14.3% less than a conventional stack of comparable overpack salvage drums.

Methods

The present subject matter provides a method of overpacking a package in overpack salvage drum 10. First, a package to be overpacked is placed into the drum body 20. This can be accomplished by lowering the package into an upright drum body 20, by placing the package onto the bottom side 202 of an upside down lid 200 and then placing the drum body 20 upside down onto the lid 200, or more typically, by laying the drum body 20 onto its side and sliding the package therein and then standing the package-filled drum body 20 upright.

In some instances, particularly when the package to be overpacked is not entirely full and/or when the package to be overpacked contains a lightweight material, the drum body 20 may have a tendency to rotate or spin relative to a surface on which it rests as the lid 200 is being threaded thereon.

To prevent the drum body 20 from rotating while the lid 200 is being threaded thereon, the bottom wall 30 of the drum body 20 may be provided with one or more grooves, for example those disclosed in U.S. Pat. No. 8,281,948 to Stanek, et al., which extend into the bottom wall 30 and across the bottom wall 30 of the drum body 20. The grooves may be sized to receive a beam, such as a wooden 2×4 or beam made of other material. In this way, an installer can stand on a beam received within a groove to prevent the drum body 20 from rotating when the lid 200 is being threaded onto the drum body.

Alternatively, a beam can be fixed to the floor and the drum body 20 can be placed onto the beam such that the beam is received in one of the grooves. The package to be overpacked can be placed into the drum body 20, either before or after the drum body has been placed onto the beam. Once the lid 200 has been secured to the drum body 20, the beam can be pulled from beneath the overpack salvage drum 10, or the overpack salvage drum 10 can be pushed off the beam.

In other embodiments where the bottom wall 30 of the drum body 20 comprises a flat exterior surface and when threading a lid thereto, an extra lid may be used in order to rotationally secure the drum body 20. For example, an extra lid can be secured to the floor and the drum body 20 can be placed onto the extra lid such that the lower side wall recesses 80 of the drum body 20 mate with the castellations 220 of the extra lid secured to the floor to rotationally secure the drum body. Another lid 200 can then be threaded on the top of the drum body to close the open top 50 of the drum body.

Once the other lid is threaded over the open top 50 of drum body to close off the interior 60 of the drum body, the overpack salvage drum 10 can be removed from the extra lid that is secured to the floor. It will be understood that instead of using an extra lid secured to the floor in order to rotationally secure the drum body, any other structure can be used that has a mating surface capable of sufficiently rotationally securing the lower side wall recesses 80 of the drum body 20.

The present subject matter also provides a method of stacking overpack salvage drums. The method optimizes safety and space concerns compared to stacking of conventional overpack salvage drums. The method can include storing and/or transporting the stack of overpack salvage drums.

In one embodiment, at least one overpack salvage drums is not sealed, wherein the lid is not engaged to the associated drum body. In another embodiment, all of the overpack salvage drums are not sealed. It will be understood that the method may include removing the lid from one or more of the drum bodies.

The method includes stacking the drum bodies so that they are nested, one within another, wherein an upper drum body fits at least partially within the interior 60 of a lower stacked drum body. The method may include for example, stacking four drum bodies, or more or less drum bodies as desired.

In one aspect, the lower side wall portion 101 of an upper stacked drum body 20 fits at least partially within the interior 60 of the lower stacked drum body. As will be understood, the upper side wall portion 100 of an upper stacked drum body 20 may not fit entirely within the interior 60 of a lower stacked drum body 20. In one aspect, the entirety of the upper side wall portion 100 of an upper stacked drum body 20 is outside the interior 60 of a lower stacked drum body 20.

As such, it will be appreciated that a total height of a stack of drum bodies may depend, at least in part, on the height of the upper side wall portion 100 for each drum body 20 in the stack. Therefore, the overall height of the stack of drum bodies may be reduced by minimizing the height of the upper side wall portion 100 of each of the drum bodies 20 to be stacked. It will be understood however, that a smallest allowable height of the upper side wall portion 100 of the drum body 20 may be limited by other considerations, such as the amount or level of stability and rigidity required or desired for the drum body 20 as provided by the upper side wall portion 100 and upper side wall recesses 110.

The method also includes stacking lids 200 one upon another, such that castellations 210 on adjacent lids are facing and are interdigitated, as shown for example in FIG. 7 between lids 200A and 200B or between lids 200C and 200D; or such that the bottom peripheral edges 350 on adjacent lids are facing, as shown for example in FIG. 7 between lids 200B and 200C. The method may include for example, stacking four, or more or less, lids as desired.

In this arrangement for a lid stack 400, the castellations 210 on adjacent lids 200 are facing so that the castellations on one lid interdigitate with castellations on another lid, wherein the castellations on one lid (e.g. lid 200A) fit in the gaps 320 between the castellations on an adjacent lid (e.g. lid 200B), and vice versa. Also, when the bottom peripheral edge 350 on adjacent lids are facing, the lugs 340 on one lid (e.g. lid 200B) fit on the lug recesses 360 on an adjacent lid (e.g. lid 200C) and vice versa. In an alternative arrangement, wherein the lids each include a projecting ring, or portion thereof on the bottom peripheral edge 350, the projecting ring, or portion thereof on one lid (e.g. lid 200B) will fit inside or outside the projecting ring, or portion thereof on an adjacent lid (e.g. lid 200C), and vice versa.

The interlocking castellations on adjacent lids, along with the reduced vertical height of each lid that is realized by incorporating the double-start female threads 250A, 250B, contribute to provide a minimal overall height 410 of the lid stack 400 as compared to the height of a stack of conventional lids having a single-start thread of comparable sealing strength and non-interlocking castellations. Furthermore, the interlocking castellations, along with the lugs and lug recesses, or ring or portions thereof, provide the added safety feature of inhibiting the stacked lids from horizontally slipping relative to each other.

The method can also include stacking the lid stack 400 on top of the stack of drum bodies. This can include engaging the bottommost lid 200A in the lid stack 400 to the topmost drum body in the drum body stack. The bottommost lid 200A can be threadingly engaged to the uppermost drum body, for example by using at least two independent lid threads and corresponding drum threads, thereby inhibiting the lid stack 400 from horizontally sliding off the drum body stack. The number of lids and drum bodies included in the stack of overpack salvage drums can be varied, and can include for example, four lids and four drum bodies or more or less of each as desired.

The present subject matter also provides a method of stacking overpack salvage drums, wherein at least one overpack salvage drum is sealed with the lid engaged to the drum body. The method can include storing and/or transporting the stack of overpack salvage drums. The method can also optionally include sealing a package in the interior of one or more of the stacked overpack salvage drums.

The method includes for at least one overpack salvage drum, sealing the lid 200 onto the drum body 20 to thereby close the overpack salvage drum 10. In one aspect, all of the overpack salvage drums are sealed. As previously described, sealing may include threadingly engaging the lid 200 to the drum body 20 by rotating the lid relative to the drum body, or vice versa. A package may be sealed in the interior 60 of one or more of the drum bodies 20 as desired.

The method includes stacking one sealed overpack salvage drum on top of another sealed overpack salvage drum as shown for example in FIGS. 1, 6, and 10 to thereby define a drum stack 1A or 1B. As shown in FIGS. 1 and 6, the bottom wall 30 of an upper overpack salvage drum 10B is within the circular cavity on (i.e. contacts) the top side 201 of the lid 200 that is sealed to the drum body 20 of the lower overpack salvage drum 10A. It will be understood that the lid 200 of the upper overpack salvaged drum 10B may optionally be sealed to the associated drum body 20.

The upper overpack salvage drum 10B is substantially vertically centered over the lower overpack salvage drum 10A, wherein the bottom wall 30 of drum 10B is within a circular cavity 380 (see FIG. 3) defined by the castellations 220, 230 and the top side 201 of the lid 200. Vertically centering the stacked overpack salvage drums relative to each other in an overpack salvage drum stack 1A can be realized through the mating of the castellations 220 having an arcuate inner facing side 221 on the lid 200 of a lower overpack salvage drum 10A, with the lower side wall recesses 80A of the upper overpack salvage drum 10B. The mating between the castellations 220 and the recesses 80 also acts to rotationally secure the upper drum body relative to the lower lid. It will be understood that the stack 1A of overpack salvage drums 10A, 10B can include more than two overpack salvage drums stacked one upon another.

Alternatively, the method can include stacking the drums such that the top sides of the lids 200 of the overpack salvage drums 10A, 10B are facing each other with interlocking castellations to thereby form a stack 1B of overpack salvage drums, as shown in FIG. 10. Like in stack 1A in FIG. 1, the upper overpack salvage drum 10B in stack 1B is substantially vertically centered over the lower overpack salvage drum 10A, and the interlocking castellations act to rotationally secure the upper lid relative to the lower lid. It will be understood that the stack 1B of overpack salvage drums 10A, 10B can include more than two overpack salvage drums stacked one upon another. For example, the first overpack salvage drum 10A can be placed on top of a third overpack salvage drum, so that the bottom wall 30 of the first overpack salvage drum 10A is contacting a top side of a lid of the third overpack salvage drum.

In one embodiment of this method, at least one of the overpack salvage drums is sealed, wherein a lid is engaged to a drum body. In another embodiment, all of the overpack salvage drums are sealed.

Many other benefits will no doubt become apparent from future application and development of this technology.

All patents, applications, standards, and articles noted herein are hereby incorporated by reference in their entirety.

The present subject matter includes all operable combinations of features and aspects described herein. Thus, for example if one feature is described in association with an embodiment and another feature is described in association with another embodiment, it will be understood that the present subject matter includes embodiments having a combination of these features.

As described hereinabove, the present subject matter solves many problems associated with previous strategies, systems and/or devices. Additional advantages and modifications will readily occur to those skilled in the art. Therefore, the present subject matter in its broader aspects is not limited to the specific details and illustrative examples shown and described herein. Accordingly, various modifications in the details, materials and arrangements of components, which have been herein described and illustrated in order to explain the nature of the present subject matter, may be made without departing from the spirit or scope of the general inventive concept as defined by the appended claims and their equivalents.

What is claimed is:

1. An overpack salvage drum comprising:
    a drum body including a bottom wall, a side wall, and an open top, the bottom wall and side wall cooperating to define an interior volume of the drum body; and
    a lid configured to close the open top of the drum body;
    wherein the lid includes a plurality of castellations that extend upwardly from a top side of the lid,
    wherein the plurality of castellations are arranged circumferentially at a periphery of the top side of the lid and are separated from each other by gaps,
    wherein when the top side of the lid is viewed in plan, the gaps separating the plurality of castellations have a larger circumferential dimension than the plurality of castellations,
    wherein the plurality of castellations comprises a first type of castellations and a second type of castellations,
    wherein the first and second types of castellations are alternatingly arranged at the periphery of the top side of the lid,
    wherein the first type of castellations extend farther in toward the center of the lid as compared to the second type of castellations, and
    wherein the drum body includes a plurality of recesses in the side wall that are configured to receive the first type of castellations when the bottom wall of the drum body contacts the top side of the lid and thereby inhibit the drum body from rotating relative to the lid.

2. The overpack salvage drum according to claim 1, wherein:
    the first type of castellations have an arcuate inner facing side; and
    the second type of castellations have a flat inner facing side.

3. The overpack salvage drum according to claim 1, wherein the second type of castellations does not contact the drum body when the bottom wall of the drum body is in contact with the top side of the lid and the first type of castellations are received in the plurality of recesses in the side wall of the drum body.

4. The overpack salvage drum according to claim 1, wherein the lid includes at least two independent lid threads configured to engage with corresponding independent drum threads provided on the drum body.

5. The overpack salvage drum according to claim 1, wherein the lid further includes:
    a skirt portion extending down from the top side of the lid and terminating at a bottom peripheral edge;
    at least one lug provided on the bottom peripheral edge; and
    at least one lug recess provided in the bottom peripheral edge;
    wherein the at least one lug recess has a size sufficient to internally receive the at least one lug.

6. The overpack salvage drum according to claim 1, wherein the gaps are aligned to receive a bar laterally across the top side of the lid.

7. A stack of overpack salvage drums comprising a first overpack salvage drum and a second overpack salvage drum, wherein:
    the first overpack salvage drum includes:
        a first drum body including a bottom wall, a side wall, a plurality of recesses in the side wall, and an open top; and
        a first lid configured to close the open top of the first drum body, the first lid including a plurality of castellations that extend upwardly from a top side of the first lid, the plurality of castellations being arranged circumferentially at a periphery of the top side of the first lid and separated from each other by gaps, wherein when the top side of the first lid is viewed in plan, the gaps separating the plurality of castellations have a larger circumferential dimension than the plurality of castellations; and
    the second overpack salvage drum includes:
        a second drum body including a bottom wall, a side wall, a plurality of recesses in the side wall, and an open top; and
        a second lid configured to close the open top of the second drum body, the second lid including a plurality of castellations that extend upwardly from a top side of the second lid, the plurality of castellations being arranged circumferentially at a periphery of the top side of the second lid and separated from each other by gaps, wherein when the top side of the second lid is viewed in plan, the gaps separating the plurality of castellations have a larger circumferential dimension than the plurality of castellations, the plurality of castellations on each of the first and second lids is a first type of castellations, each of the first and second lids further comprises a second type of castellations, the first and second types of castellations are alternatingly arranged at the periphery of the top side of each of the first and second lids and separated from each other by gaps, the first type of castellations extend farther in toward the center of each of the first and second lids as compared to the second type of castellations on each of the first and second lids, and the plurality of recesses in the side wall of each of the first and second drum bodies are configured to receive the first type of castellations on each of the first and second lids when the bottom wall of the drum body of the one of the overpack salvage drums contacts the top side of the lid of the other of the overpack salvage drums and thereby inhibit the drum body of the one overpack salvage drum from rotating relative to the lid of the other overpack salvage drum.

8. The stack according to claim 7, wherein:
the first overpack salvage drum is sealed;
the top side of the first lid is contacting the bottom wall of the second drum body; and
the first type of castellations of the first lid are received within recesses in the side wall of the second drum body.

9. The stack according to claim 8, wherein:
the first type of castellations have an arcuate inner face; and
the second type of castellations having a flat inner face.

10. The stack according to claim 8, wherein the second type of castellations of the first lid do not engage the second drum body.

11. The stack according to claim 7, wherein each of the first and second lids and each of the first and second drum bodies includes at least two independent lid threads.

12. The stack according to claim 7, wherein:
the first overpack salvage drums is not sealed; and
the plurality of castellations of the first lid are received in the gaps between the plurality of castellations of the second lid.

13. The stack according to claim 7, wherein:
each of the first and second lids further includes a skirt portion extending down from the top side and terminating at a bottom peripheral edge, the bottom peripheral edge including at least one lug and at least one lug recess;
the at least one lug recess on the first lid has a size sufficient to internally receive the at least one lug on the second lid; and
the at least one lug recess on the second lid has a size sufficient to internally receive the at least one lug on the first lid.

14. The stack according to claim 13, wherein:
the first and second overpack salvage drums are not sealed;
the bottom peripheral edge of the first lid is facing the bottom peripheral edge of the second lid;
the at least one lug recess of the first lid internally receives the at least one lug of the second lid; and
the at least one lug recess of the second lid internally receives the at least one lug of the first lid.

\* \* \* \* \*